United States Patent [19] [11] Patent Number: 4,998,917
Gaiser et al. [45] Date of Patent: Mar. 12, 1991

[54] HIGH TORQUE STEERABLE DILATATION CATHETER

[75] Inventors: John W. Gaiser; Abdul-Razaq A. Balogun, both of Mountain View, Calif.

[73] Assignee: Advanced Cardiovascular Systems, Inc., Santa Clara, Calif.

[21] Appl. No.: 287,772

[22] Filed: Dec. 21, 1988

Related U.S. Application Data

[63] Continuation-in-part of Ser. No. 199,099, May 26, 1988, Pat. No. 4,940,062.

[51] Int. Cl.$^5$ ............................................. A61M 29/00
[52] U.S. Cl. ..................................... 604/96; 606/194
[58] Field of Search .............................. 606/192–194; 604/95–103, 164, 282; 128/656–658, 772

[56] References Cited
U.S. PATENT DOCUMENTS 4,616,653 10/1986 Samson et al. .......................... 604/95
4,771,778 9/1988 Mar ......................................... 604/96
4,784,636 11/1988 Rydell ..................................... 604/22
4,793,350 12/1988 Mar et al. ............................... 604/96
4,838,268 6/1989 Keith et al. ............................ 604/96
4,884,573 12/1989 Wijay et al. ........................... 128/344

Primary Examiner—C. Fred Rosenbaum
Assistant Examiner—William W. Lewis
Attorney, Agent, or Firm—Fulwider, Patton, Lee & Utecht

[57] ABSTRACT

A steerable dilatation catheter which is particularly adapted for angioplasty procedures having a concentric construction of thin-walled inner and outer tubular members of high strength plastic, such as polyimide, which provide diametric rigidity but longitudinal flexibility. At least the distal portion of the inner and outer tubular members which will extend out of the guiding catheter during angioplasty procedures have wall thicknesses of less than 0.002 inch, preferably less than 0.0015 inch. An elongated core member is adapted to freely rotate within the inner tubular member but is prevented from any significant axial movement therein.

19 Claims, 1 Drawing Sheet

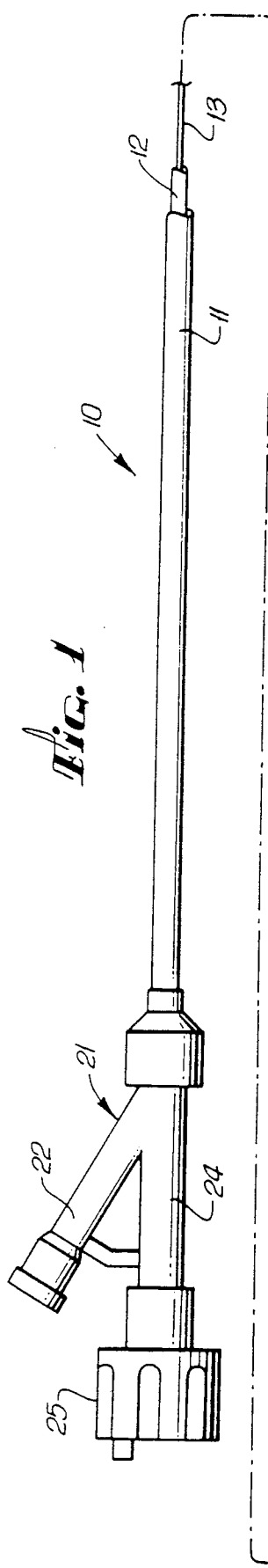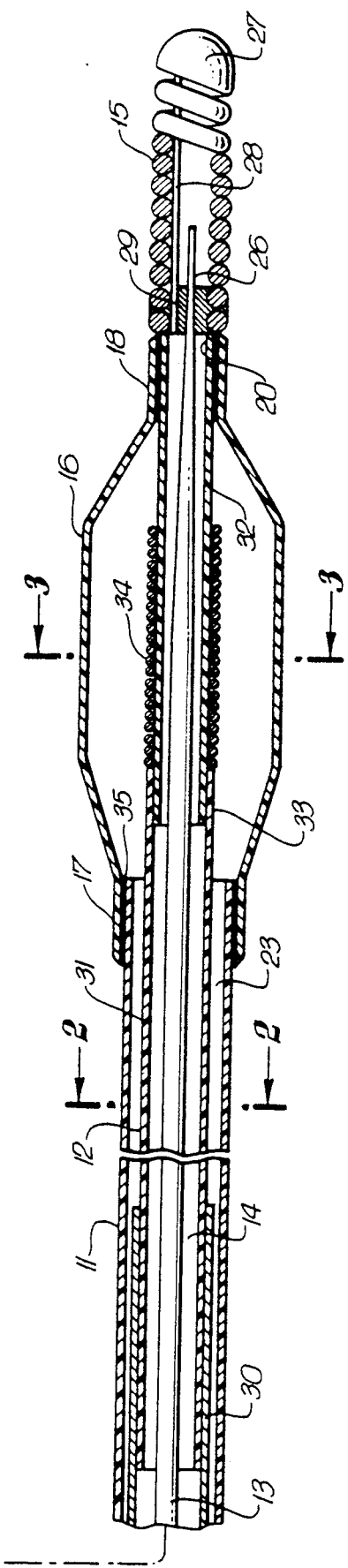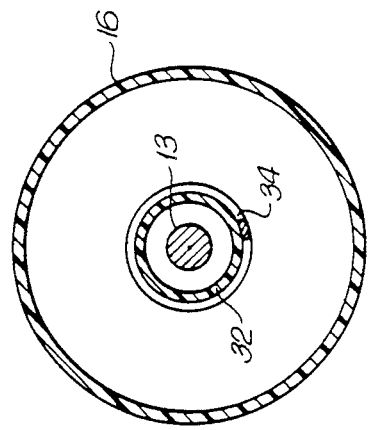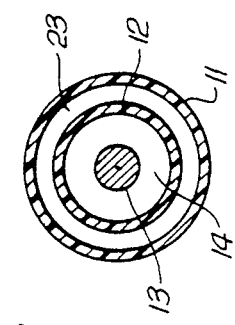

ns severely
HIGH TORQUE STEERABLE DILATATION CATHETER

RELATED APPLICATIONS

This application is a continuation-in-part application of U.S. application Ser. No. 199,099, filed May 26, 1988, now U.S. Pat. No. 4,940,062.

BACKGROUND OF THE INVENTION

This invention generally relates to vascular catheters and particularly low-profile steerable catheters for angioplasty procedures, such as percutaneous transluminal coronary angioplasty (PTCA).

In classic PTCA procedures, a dilatation catheter having an inflated balloon on the distal end thereof is advanced through a patient's arterial system until the deflated balloon crosses the atherosclerotic lesion to be dilated. The balloon is inflated to a predetermined size with radiopaque liquid at relatively high pressures to compress the atherosclerotic plaque against the inside of the artery wall and then the balloon is deflated so that the catheter can be removed and blood flow resumed.

Typically, a guiding catheter having a preformed distal end is first percutaneously introduced into the patient's arterial system with the distal tip in the coronary artery. A guidewire is advanced through the guiding catheter into the patient's coronary anatomy until the distal end of the guidewire crosses the lesion to be dilated. The dilatation catheter is then advanced over the guidewire, with the guidewire slidably disposed within an inner lumen of the catheter, until the inflatable balloon is positioned across the lesion so that the balloon can dilate the lesion when it is inflated. For a more detailed description of angioplasty procedures and the devices used in such procedures, reference is made to U.S. Pat. No. 4,323,071 (Simpson-Robert); U.S. Pat. No. 4,332,254 (Lundquist); U.S. Pat. No. 4,439,185 (Lundquist); U.S. Pat. No. 4,468,224 (Enzmann et al.) U.S. Pat. No. 4,516,972 (Samson); U.S. Pat. No. 4,538,622 (Samson et al.); and U.S. Pat. No. 4,616,652 (Simpson) which are hereby incorporated herein in their entirety.

Steerable dilatation catheters with built-in or fixed guidewires or guiding elements are being used with greater frequency because the deflated profile of such catheters are generally much smaller than conventional dilatation catheters having the same inflated balloon size. Further details of low-profile steerable dilatation catheters may be found in U.S. Pat. No. 4,582,181 (Samson) which is hereby incorporated in its entirety by reference thereto. The lower profile of these catheters allows the catheter to cross tighter lesions and to be advanced much deeper into the patient's coronary anatomy. Moreover, the use of steerable low-profile dilatation catheters having a built-in guidewire or guiding element shortens considerably the time for the angioplasty procedures because there is no need to first insert a guidewire and then insert a conventional dilatation catheter over the previously inserted guidewire.

However, it has been found that the balloon elements of commercially available very low-profile steerable catheters tend to wrap on themselves when the catheter is torqued so that the balloon frequently will not completely inflate when positioned across a stenosis or if inflated to deflate within a desired time period. Some suppliers of such catheters recommend that the catheter be limited to one rotation to avoid such balloon wrapping. However, such restrictions on rotations severely limit the steerability of the catheter within a patient's vasculature.

What has been needed and heretofore unavailable is a steerable dilatation catheter having a very low profile which can be torqued from the proximal end thereof without wrapping the inflatable balloon element. The present invention satisfies this and other needs.

SUMMARY OF THE INVENTION

This invention is directed to a steerable dilatation catheter having excellent pushability and a very low profile.

The steerable dilatation catheter in accordance with the present invention includes a thin-walled, outer tubular member, a thin-walled inner tubular member disposed within the outer tubular member, an inflatable balloon member secured by the proximal end thereof to the distal end of the outer member and by the distal end thereof to the distal end of the inner tubular member, and a core member extending through the inner lumen of the inner tubular member and out of the distal end thereof. An elongated flexible body such as a helical coil is disposed about the distal portion of the core member which extends out of the distal end of the inner tubular member.

At least the distal portion of the inner tubular member is formed of plastic material which provided longitudinal flexibility and diametric rigidity and has a wall thickness less than 0.0015 inch, preferably less than 0.00125 inch. The outer tubular member is also formed of plastic material which provides longitudinal flexibility and diametric rigidity and has a wall thickness less than 0.002 inch, preferably less than 0.0015 inch.

The distal portion of the inner tubular member which is disposed in that portion of the catheter which extends out of the guiding catheter during angioplasty procedures into the patient's coronary artery is preferably formed of high strength plastic material such as polyimide. Wall thicknesses less than 0.0006 inch generally do not provide sufficient strength for use within a patient's vascular system. In a preferred embodiment, the inner tubular member is formed of a hypotubing except for the distal section formed of polyimide. Stainless steel, nitinol and other hypotubing may be employed.

The structure of the catheter tip distally of the balloon may be of a floppy design wherein the distal tip of the core member extends into a coil or other elongated flexible body but terminates short of the distal tip thereof. A shaping ribbon extends from the portion of the core member extending out of the distal end of the inner tubular member to the distal tip of the coil or flexible body where it is secured to a radiopaque plug. Alternately, the structure of the distal tip of the catheter may be a standard design, wherein the distal tip of the core member extends distally through the interior of the coil and is secured to the radiopaque plug in the distal tip thereof. The distal tip of the catheter is preferably deflectable by means operable from the proximal end of the catheter, such as described in copending application Ser. No. 199,099, filed May 26, 1988, which is incorporated herein it its entirety by reference thereto.

The proximal end of the catheter is provided with a multi-arm adapter having means to introduce inflation fluid into the annular lumen disposed between the inner and outer tubular members and means to apply torque to the core member disposed within the inner lumen of the inner tubular member in order to provide steerability to the dilatation catheter. The core member is free to rotate within the inner lumen of the inner tubular member, but means are provided to prevent significant axial movement of the core within the inner lumen of the inner tubular member.

In accordance with the invention, both ends of the inflatable balloon are fixed so there is little or no tendency for the balloon to wrap on itself when the catheter is steered through a patient's tortuous arterial system, particularly the coronary anatomy thereof.

These and other advantages of the dilatation catheter of the invention will become more apparent from the following detailed discussion thereof when taken in conjunction with the accompanying exemplary drawings.

BRIEF DESCRIPTION OF THE DRAWINGS

FIG. 1 is an elevational view, partially in section, of the steerable dilatation catheter embodying features of the invention;

FIG. 2 is a transverse cross-sectional view of the catheter shown in FIG. 1 taken along the line 2—2; and FIG. 3 is a transverse cross-sectional view of the catheter shown in FIG. 1 taken along the lines of 3—3.

DETAILED DESCRIPTION OF THE INVENTION

FIG. 1 illustrates a steerable dilatation catheter assembly 10 generally comprising a thin-walled, outer tubular member 11, a thin-walled inner tubular member 12, a core wire or member 13 disposed within the inner lumen 14 of inner tubular member 12 with a flexible coil 15 on the distal portion thereof and inflatable relatively inelastic balloon member 16 which is secured by suitable adhesives at the proximal end 17 thereof to the distal end of the outer tubular member 11 and at the distal end 18 thereof to the distal end 20 of the inner tubular member 12. A multi-arm adapter 21 is provided on the proximal end of the catheter assembly 10 and is secured to the proximal ends of both the outer tubular member 11 and the inner tubular member 12. Arm 22 of adapter 21 is in fluid communication with the annular lumen 23 disposed between the outer and inner tubular members 11 and 12, respectively, and is adapted to direct inflation fluid therethrough to the interior of balloon member 16. Arm 24 is adapted to receive the proximal end (not shown) of the core wire 13 and has a torquing knob 25 secured to the end of the core wire 13 in order to rotate the core wire within the inner lumen 14 of the inner tubular member 12 and thereby rotate the distal portion thereof having flexible core 15 secured thereto. In this manner, the catheter assembly 10 can be steered through the patient's tortuous coronary anatomy.

In the presently preferred embodiment shown in FIG. 1, the portion of the catheter assembly 10 distal to the balloon member 16 is provided with a floppy construction wherein the distal end of the core member 13 terminates short of the distal tip of the coil 15 and a shaping ribbon 28 extends to the plug 27 in the distal tip of the flexible coil 15 and is secured thereto. The proximal end of the shaping ribbon 28 is secured to the distal portion of the core member 13 by suitable means, such as brazing, soldering, welding, or adhesives at location 29.

At least those portions of the outer and inner tubular members 11 and 12, respectively, which are disposed in that portion of the catheter assembly 10 which extends out of the distal end of a guiding catheter into a patient's coronary arteries during angioplasty procedures are formed of suitable high-strength plastic material, such as polyimide which provides a thin-walled construction with diametric rigidity to avoid kinking or buckling of the tubular members but with sufficient longitudinal flexibility to pass through a patient's tortuous coronary anatomy. Generally, the wall thickness of both the outer and inner tubular members 11 and 12 are less than about 0.002 inch, preferably less than about 0.0015 inch. In the portions of the inner member 12 within the interior of the balloon member 16 and distal thereto, the wall thickness is preferably less than about 0.001 inch. At least the most distal 20 cm, preferably 30 cm, of the outer and inner tubular members 11 and 12, respectively, has the thin-walled construction of the invention.

The inner tubular member 12 preferably has a proximal section 30 formed of a hypotubing from material such as stainless steel, nitinol and the like to provide pushability and an intermediate section 31 and a distal section 32 are formed of polyimide tubing. The proximal end of the intermediate member 31 interfits with the open distal end of the proximal section 30 and the proximal end of distal section 32 interfits with the open distal end of the intermediate section 31. The interfitting ends of sections 30, 31, and 32 are secured together by adhesives or other suitable means. The intermediate and distal sections 31 and 32 of the inner tubular member 12 are in that section of the catheter assembly 10 which extends out of the guiding catheter. Therefore, the combined length of sections 31 and 32 should be greater than about 20 cm, preferably greater than about 30 cm.

As shown in FIG. 1, the transition section 33 between the intermediate section 31 and the distal section 32 is followed distally by a radiopaque marker coil 34 which preferably has a thickness the same as or slightly less than the wall of the intermediate section and the same length as the operative portion of the balloon member 16.

The outer tubular member 11 is preferably formed of polyimide over essentially its entire length. Thin-walled sections of other materials can also be included.

The core member 13 which is disposed within the inner lumen 14 of inner tubular member 12 has a diameter over most of its length which is just slightly less than the diameter of the inner lumen 14 in order to reduce the profile of the catheter as much as possible. In addition, the small differential between the OD of the core member 13 and the ID of the inner tubular member 12 allows for common support therebetween. Differentials between the ID and the OD should be less than about 0.0025 inch, preferably less than about 0.0015 inch. The diameter of the core member 13 is less than about 0.012 inch over most of its length. Typically, the core member has a plurality of sections of various diameters, e.g., a proximal section having a diameter of about 0.008 to about 0.012 inch and a length of about 120 to about 160 cm; an intermediate section having a diameter of about 0.004 to about 0.008 inch and a length of about 8 to about 20 cm; and a distal section having a diameter of about 0.002 to about 0.004 and a length of about 4 to about 10 cm. Generally tapers of about 1 to about 4 cm in length are provided between the core member sections. The distal tip of the distal section of core member 13 may be flattened to a thickness of about 0.001 inch if it is to extend to the distal tip of plug 27 as is characteristic of standard or non-floppy construction. While the presently preferred embodiment of the core member 13 is a solid member of stainless steel, all or part of the core member 13 may be formed of material such as nitinol and the like. Moreover, the core member may be formed as a tubular member with one or more openings within the coil member to take pressure measurements therein and to deliver fluids, including drugs.

The balloon member 16 is preferably a thin-walled, flexible but relatively inelastic member which is secured at the proximal end 17 to the distal end of the outer tubular member 11 by a suitable adhesive 35 (e.g., a UV cured epoxy or cyanoacrylate) and the distal end 18 of balloon 16 is secured by the same or similar adhesive 36 to the distal end of inner member 12. The balloon may be made of a wide variety of flexible, relatively inelastic biaxially oriented plastic materials such as polyolefins, including polyethylene and polyethylene terephthalate. The thickness of the balloon wall in the operative or cylindrical portion thereof should be less than about 0.0015 inch, preferably less than 0.0015 inch.

The flexible coil 15 on the distal portion of the catheter assembly 10 is secured to the freely rotating core member 13 so as not to restrict the rotation thereof. However, the outer diameter of the flexible coil 15 is usually larger than the ID of the inner tubular member 12 in order to restrict axial movement of the core member 13 and the flexible coil member 15 secured thereto in the proximal direction. The torque knob 25 on the proximal end of the core member 13 restricts axial movement thereof in the distal direction, but it does not restrict the number of turns which may be given to the core member 13 secured thereto.

The flexible coil 15 may be formed from a stainless steel wire or other suitable wire product, such as palladium, platinum, and alloys thereof including small quantities of molybdenum. The shaping ribbon 28 is preferably a cold worked ribbon of tungsten-rhenium alloy.

The catheter assembly of the present invention has excellent flexibility in at least the distal portion thereof which extends out of the guiding catheter and into a patient's coronary arteries during angioplasty procedures. However, notwithstanding this flexibility, the catheter has excellent pushability so that it can be readily advanced across tight stenoses. The inflation and deflation of the balloon is rapid to enhance safety during the dilatation process.

The presently preferred thin-walled polyimide tubing is the MICRO-BORE TM tubing manufactured by PolyMicro Technologies of Phoenix, Ariz. Another desirable tubing is manufactured by H.V. Technologies of Trenton, Ga. Further information regarding polyimide material may be found in THE HANDBOOK OF THERMOSET PLASTICS, Chapter 8, "Commercial Polyimides," edited by Sidney H. Goodman (1986), and an article by E. Sacher entitled "A Reexamination of Polyimide Formation," J. MACROMOLECULAR SCIENCE-PHYSICS, Vol. B25, No. 4 (1986) pp 405–418 which are hereby incorporated by reference thereto. Polyimide tubing having a wall thickness of less than about 0.002 inch preferably within the range of 0.0006 to about 0.0015 inch provides the mechanical and physical properties comparable to a conventionally used polyethylene and polyvinylchloride products which have wall thicknesses many times greater, e.g., 0.005 inch. Preferably, suitable means to vent air from the interior of the balloon member are provided such as described in U.S. Pat. No. 4,692,200; U.S. Pat. No. 4,638,805; and copending application Ser. No. 000,651 filed Jan. 6, 1987, all of which are incorporated herein by reference thereto.

While the description of the present invention is directed herein to certain preferred embodiments, it is obvious that various modifications and improvements can be made thereto without departing from the scope thereof.

What is claimed is:

1. A steerable balloon dilatation catheter suitable for angioplasty procedures, comprising:
    (a) a thin-walled tubular outer member formed of plastic material having an inner lumen extending therethrough;
    (b) a tubular inner member disposed within the inner lumen of the outer tubular member and having an inner lumen extending therethrough with an axial opening at the distal tip thereof with a distal tubular portion of the inner tubular member having a thin wall and being formed of high strength plastic material providing longitudinal flexibility and diametric rigidity and a proximal tubular portion being formed of hypotubing to provide improved pushability;
    (c) an inflatable, relatively inelastic balloon member on the distal portion of the catheter assembly with the proximal end of the balloon member being sealingly secured to the distal end of the outer tubular member, the distal end of the balloon member being sealingly secured to the distal end of the inner member and the interior of the balloon member being in fluid communication with an annular lumen disposed between the inner and outer tubular members; and
    (d) an elongated core member disposed within the inner lumen of the inner tubular member with a distal portion thereof extending out of the axial opening in the distal tip thereof and having a flexible body disposed therearound, said core member being axially rotatable within the inner lumen of the inner member but fixed to prevent significant longitudinal movement of the core member within said inner lumen.

2. The dilatation catheter of claim 1 including an adapter on the proximal end thereof having the proximal ends of the inner and outer members secured thereto, means to torque the core member rotatably disposed within the inner lumen of the inner tubular member and means to direct inflation fluid into the interior of the balloon member through the annular inner lumen between the inner and outer tubular members.

3. The dilatation catheter of claim 1 wherein the wall thickness of the distal portion of the inner member is less than about 0.002 inch.

4. The dilatation catheter of claim 1 wherein the wall thickness of the distal portion of the inner tubular member is less than about 0.0015 inch.

5. The dilatation catheter of claim 1 wherein the distal portion of the inner tubular member is formed of polyimide and is at least 20 cm. in length.

6. The dilatation catheter of claim 1 wherein the wall thickness of the outer tubular member is less than about 0.0015 inch.

7. The dilatation catheter of claim 1 wherein the outer tubular member has a distal section which is formed of polyimide and which is at least 20 cm. in length.

8. The dilatation catheter of claim 1 wherein the flexible body secured to the distal tip of the core member is a coil formed of a material selected from the group consisting of palladium, platinum, and alloys thereof.

9. The dilatation catheter of claim 8 wherein the coil is formed of an alloy of palladium, platinum and molybdenum.

10. The dilatation catheter of claim 1 wherein the flexible body is a coil and the distal end of the core member extends into the coil but terminates short of the distal tip thereof.

11. The dilatation catheter of claim 10 wherein a shaping ribbon is disposed within the coil with the proximal end thereof being secured to the distal end of the core member and the distal end of the shaping ribbon extending and secured to the distal tip of the coil.

12. The dilatation catheter of claim 1 wherein the diameter of the inner lumen in the distal portion of the inner tubular member is less than about 0.012 inch.

13. The dilatation catheter of claim 1 wherein the diameter of the inner lumen of the inner tubular member is about 0.006 to about 0.011 inch.

14. The dilatation catheter of claim 1 wherein the balloon member has a wall thickness of less than 0.001 inch.

15. The dilatation catheter of claim 14 wherein the balloon member is formed of polyethylene terephthalate.

16. The dilatation catheter of claim 1 including means operable from the proximal end of the catheter to deflect the flexible body.

17. The dilatation catheter of claim 1 wherein the distal portion of the inner tubular member includes proximal and distal tubular sections and the proximal section has a larger outer diameter than the outer diameter of the distal section thereof.

18. The dilatation catheter of claim 17 wherein the proximal and distal sections are formed of polyimide.

19. The dilatation catheter of claim 18 wherein the distal section has a proximal end which interfits and is secured within the distal end of the proximal section.

* * * * *